United States Patent [19]

Nakajima et al.

[11] Patent Number: 5,062,922

[45] Date of Patent: Nov. 5, 1991

[54] SIZING PAPER WITH α-HYDROXYCARBOXYLIC ACID

[75] Inventors: Masato Nakajima; Kenji Yokotani, both of Hirakata; Atsushi Ikeda, Osaka, all of Japan

[73] Assignee: Arakawa Kagaku Kogyo Kabushiki Kaisha, Osaka, Japan

[21] Appl. No.: 411,123

[22] Filed: Sep. 22, 1989

Related U.S. Application Data

[63] Continuation-in-part of Ser. No. 180,922, Apr. 13, 1988, abandoned.

[30] Foreign Application Priority Data

Dec. 24, 1987 [JP] Japan ................................. 62-327932

[51] Int. Cl.$^5$ ............................................ D21H 17/14
[52] U.S. Cl. ................. 162/158; 162/168.1; 162/174; 162/175; 162/179
[58] Field of Search ............... 162/158, 179, 174, 175, 162/168.1; 106/243

[56] References Cited

U.S. PATENT DOCUMENTS

| | | | |
|---|---|---|---|
| 2,692,183 | 10/1954 | Ericks | 162/158 |
| 3,954,581 | 5/1976 | Carlin | 204/128 |
| 4,529,762 | 7/1985 | Hoefer et al. | 524/157 |
| 4,673,439 | 6/1987 | Takahashi et al. | 106/287.24 |

OTHER PUBLICATIONS

Rapport et al, "The Lipid Residues in Cytolipin H*", *J. Lipid Research* (Apr. 1961), vol. 2, No. 2, pp. 148–151.
*Chem. Ber.*, 87 (1954), 1058–1060.
Cooper et al, "Surface Active Properties of Biosurfactant from Corynebacterium Lepus", *JAOCS* (Jan. 1981), pp. 77–80.

*Primary Examiner*—Peter Chin
*Attorney, Agent, or Firm*—Armstrong, Nikaido, Marmelstein, Kubovcik & Murray

[57] ABSTRACT

A method for making papers which comprises: using a paper sizing agent comprising as an effective component an α-hydroxycarboxylic acid having the formula (I):

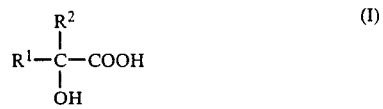

wherein $R^1$ is an alkyl group having 8 to 30 carbon atoms, an alkenyl group having 8 to 30 carbon atoms,

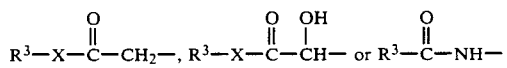

and $R^2$ is hydrogen atom, or an alkyl or alkenyl group having 1 to 30 carbon atoms, or a salt thereof. The paper sizing agent used in the method can exhibit the excellent sizing effect in paper making under the condition of the wide pH-range from pH 3 to pH 9, and has an excellent storage stability. Further the method is excellent in workability and high in industrial value.

12 Claims, No Drawings

SIZING PAPER WITH α-HYDROXYCARBOXYLIC ACID

CROSS-REFERENCE TO RELATED APPLICATION

This is a continuation-in-part of application Ser. No. 180,922 filed on Apr. 13, 1988 abandoned.

BACKGROUND OF THE INVENTION

The present invention relates to a method for sizing papers, and more particularly to a method for sizing papers using a paper sizing agent which can be used under a condition of a wide pH-range from acidic to alkaline conditions.

In a conventional method of paper making under an acidic condition (hereinafter referred to as "acidic paper making"), there have been suitably used as sizing agents, soaps or dispersions of fortified rosins, soaps of fatty acids, hydrolyzed addition products of an olefine oligomer with succinic anhydride, and the like. However, the acidic paper making involves defects such that paper machines are corroded and the strength and durability of the obtained paper are deteriorated with the passage of time.

On the other hand, a paper making under an alkaline condition (hereinafter referred to as "alkaline paper making") has no defects in the acidic paper making. Therefore, various compounds have been studied for obtaining a sizing agent suitable for use in the alkaline paper making. However, it is impossible to exhibit a satisfactory sizing effect in practical use, when using the sizing agents used in the acidic paper making as the sizing agent used in the alkaline paper making.

Further, though typical sizing agents for the alkaline paper making such as an alkenyl succinic anhydride sizing agent and an alkyl ketene dimer sizing agent have been developed, these sizing agents have the following defects.

That is, the alkenyl succinic anhydride sizing agent is poor in workability, since it cannot be stored in the state of an aqueous dispersion due to the poor hydrolysis resistance, therefore it is necessary to emulsify or disperse the sizing agent just before it is added to the paper furnish. Also, the alkyl ketene dimer sizing agent has a disadvantage that the sizing effects immediately after the end of the paper making are poor since it takes a long time to exhibit the satisfactory sizing effect. Of course, these sizing agents cannot be used in the acidic paper making using aluminum sulfate as a fixing agent.

As aforementioned, the known sizing agents can be only used in the method of paper making under the condition of the specific range of pH, and there has not yet been proposed a sizing agent capable of applying to the methods of paper making under from acidic to alkaline conditions. Accordingly, it has been desired to be developed a sizing agent which has no defects mentioned above and can be used in the paper making under a condition of a wide range of pH.

An object of the present invention is to provide a method for sizing papers using a sizing agent which does not have the above-mentioned defects, is satisfactory in the sizing effect and the workability, and can be used in the method of paper making under a condition of a wide pH-range from acidic to alkaline conditions.

The above and other objects of the present invention will become apparent from the description hereinafter.

SUMMARY OF THE INVENTION

It has now been found that when a specific α-hydroxycarboxylic acid is used as an effective component in a sizing agent, there can be provided a paper sizing agent which has the excellent sizing effect and storage stability, and can be used in paper making methods under a condition of a wide pH-range from acidic to alkaline conditions.

That is, in accordance with the present invention, there is provided a method for sizing papers which comprises: using a paper sizing agent comprising as an effective component an α-hydroxycarboxylic acid having the formula (I):

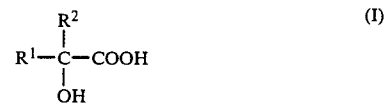

wherein $R^1$ is an alkyl group having 8 to 30 carbon atoms, an alkenyl group having 8 to 30 carbon atoms, a group having the formula (IIa):

in which $R^3$ is an alkyl group having 8 to 30 carbon atoms or an alkenyl group having 8 to 30 carbon atoms and X is an oxygen atom or —NH—, a group having the formula (IIb):

in which $R^3$ and X are as defined above, or a group having the formula (IIc):

in which $R^3$ is as defined above; and $R^2$ is a hydrogen atom, an alkyl group having 1 to 30 carbon atoms or an alkenyl group having 1 to 30 carbon atoms; or a salt thereof.

DETAILED DESCRIPTION

In the present invention, an α-hydroxycarboxylic acid having the formula (I):

or a salt thereof is used as an effective component of the paper sizing agent.

In the above-mentioned formula (I), $R^1$ is an alkyl group having 8 to 30, preferably 12 to 26, more preferably 16 to 22, carbon atoms; an alkenyl group having 8 to 30, preferably 12 to 26, more preferably 16 to 22, carbon atoms; a group having the formula (IIa):

(IIa)

in which $R^3$ is an alkyl group having 8 to 30, preferably 12 to 26, more preferably 16 to 22, carbon atoms or an alkenyl group having 8 to 30, preferably 12 to 26, more preferably 16 to 22, carbon atoms, and X is an oxygen atom or —NH—; a group having the formula (IIb):

(IIb)

in which $R^3$ and X are as defined above; or a group having the formula (IIc):

(IIc)

in which $R^3$ is as defined above; and $R^2$ is a hydrogen atom, an alkyl group having 1 to 30, preferably 1 to 26, more preferably 1 to 22, carbon atoms or an alkenyl group having 1 to 30, preferably 1 to 26, more preferably 1 to 22, carbon atoms.

Examples of the α-hydroxycarboxylic acid are, for instance, an α-hydroxyalkanoic acid such as 2-hydroxypalmitic acid, 2-hydroxystearic acid, 2-hydroxybehenic acid or 2-hydroxymyristic acid, a dialkyl hydroxyacetic acid such as dipentadecyl hydroxyacetic acid or diheptadecyl hydroxyacetic acid, a monoester of malic acid (hydroxysuccinic acid) such as 2-hydroxy-3-hexadecyloxycarbonylpropionic acid or 2-hydroxy-3-octadecyloxycarbonylpropionic acid, a monoester of tartaric acid (dihydroxysuccinic acid) such as 2,3-dihydroxy-3-hexadecyloxycarbonylpropionic acid or 2,3-dihydroxy-3-octadecyloxycarbonylpropionic acid, an amido glycolic acid such as N-(hydroxycarboxy)methylpalmitamide, or N-(hydroxycarboxy)methylstearamide, and the like. The α-hydroxycarboxylic acids may be used alone or as an admixture thereof. Also, salts of the α-hydroxycarboxylic acid such as its alkali metal salts, ammonium salts or alkanolamine salts can be used.

The α-hydroxycarboxylic acid (I) used in the invention can be prepared in a known synthesizing method.

The α-hydroxyalkanoic acids such as 2-hydroxystearic acid can be easily prepared by, for instance, a method in which an addition reaction of stearic acid and bromine is carried out in the presence of red phosphorus as a catalyst and the reaction product is hydrolyzed with an alkali such as sodium hydroxide. For purifying it, a method disclosed in Journal of Lipid Research (J. Lipid. Res.), 2, 148(1961) can be adopted.

The dialkyl hydroxyacetic acids such as dipentadecyl hydroxyacetic acid and diheptadecyl hydroxyacetic acid can be prepared according to a method, for example, disclosed in Chemische Berichte (Chem. Ber.), 87, 1058–1060(1954).

The monoesters of malic acid having the formula (I) wherein $R^1$ is the group (IIa) and $R^2$ is hydrogen, such as 2-hydroxy-3-hexadecyloxycarbonylpropionic acid and 2-hydroxy-3-octadecyloxycarbonylpropionic acid can be prepared by, for instance, a method in which to dioxane are added malic acid and an alkanol in a molar ratio of about 3:1, the mixture is refluxed for several hours, and then dioxane is distilled away under reduced pressure to give a product. To the obtained product is added an organic solvent such as toluene. After the unreacted malic acid which is indissoluble in toluene is recovered from the mixture, the mother liquor is concentrated under reduced pressure. The obtained product contains two kinds of isomers which are different from each other in the position of the esterified carboxyl group in the product in the ratio of about 1:1 as main components, and a small amount of its diester. The obtained product as it is or the monoester obtained by purifing the product and isolating therefrom can be used as the paper sizing agent of the invention.

The monoesters of tartaric acid having the formula (I) wherein $R^1$ is the group (IIb) and $R^2$ is hydrogen, such as 2,3-dihydroxy-3-hexadecyloxycarbonylpropionic acid and 2,3-dihydroxy-3-octadecyloxycarbonylpropionic acid can be prepared in the same manner as in the preparation of the monoesters of malic acid. That is, to dioxane are added tartaric acid and an alkanol in a moler ratio of about 3:1, the mixture is refluxed for about 6 hours in the presence of p-toluenesulfonic acid as a catalyst, and then dioxane is distilled away under reduced pressure to give a product. The unreacted tartaric acid is removed from the reaction mixture to give a desired product.

The amido glycolic acids having the formula (I) wherein $R^1$ is the group (IIc) and $R^2$ is hydrogen such as N-(hydroxycarboxy)methylpalmitamide and N-(hydroxycarboxy)methylstearamide can be prepared by for example, dissolving a fatty acid amide in a solvent such as tetrahydrofuran with heat, adding monohydrate of glyoxylic acid to the mixture and reacting it at a temperature of about 60° C. for 4 hours, then recrystallizing from the reaction mixture.

The thus obtained α-hydroxycarboxylic acid (I) is dispersed into water to give an aqueous dispersion containing the α-hydroxycarboxylic acid (I) as the effective component, namely, the sizing agent of the present invention.

As a dispersing method, usual methods such as a high pressure emulsifying method and a phase-inversion method are adopted. According to the high pressure emulsifying method, the α-hydroxycarboxylic acid (I) is melted or it is dissolved in a solvent such as benzene or toluene, to which an emulsifier and warm water having a temperature of 60° to 100° C. are added, then the mixture is emulsified by using a high pressure homogenizer. The obtained aqueous dispersion as it is as well as an aqueous dispersion obtained by distilling away the solvent can be used.

In case of the phase-inversion method, after the α-hydroxycarboxylic acid (I) and the emulsifier are thoroughly kneaded and melted, to which warm water having a temperature of 60° to 100° C. is gradually added dropwise with stirring under the melting state to conduct the phase inversion, thereby obtaining an aqueous dispersion without using a solvent or a special homogenizer.

Usual emulsifiers can be used in the present invention without any particular limitation and various surfactants and protective colloids can be used. Examples of the surfactants are, for instance, anionic surfactants such as an alkylbenzenesulfonate, an alkylsulfate, a rosined soap, a polyoxyethylene alkylphenyl ether sulfate, polyoxyethylene alkylphenyl ether sulfonate, polyoxyethylene alkylphenyl ether sulfosuccinate, a polyoxyethylene distyrylphenyl ether sulfate and a polyoxyethylene distyrylphenyl ether sulfosuccinate; nonionic surfactants such as polyethylene oxide, polypropylene oxide, and an alkyl, aryl, alkylaryl or aralkylaryl ester or partial ester, ether, or amide of polyethylene oxide or polypropylene oxide; cationic surfactants such as lauryltrimethylbenzylammonium chloride, stearyltrimethylbenzylammonium chloride, distearyldimethylammonium chloride, alkylbenzyldimethylammonium chloride and alkylpyridinium chloride and the like. Examples of the protective colloids are, for instance, casein, lecithin, polyvinyl alcohol, a salt of styrene-maleic anhydride copolymer, a salt of styrene-acrylic acid copolymer, various kinds of modified starches, and the like.

As the sizing agent there can be used an aqueous solution of the salt of α-hydroxycarboxylic acid (I) obtained by neutralizing the acid (I) with a hydroxide of an alkali metal, ammonium or an alkanol amine as well as the aqueous dispersion of the α-hydroxycarboxylic acid (I) as mentioned above.

In the present invention, water is added to the mixture of 80 to 99% by weight, preferably from 85 to 98% by weight, of the α-hydroxycarboxylic acid (I) and 20 to 1% by weight, preferably from 15 to 2% by weight of the emulsifier to give the aqueous dispersion or solution. Thus obtained aqueous dispersion or solution has a solid content of 0.5 to 70% by weight, preferably from 0.5 to 50% by weight.

Further, a fixing agent, as mentioned later, can be mixed with the α-hydroxycarboxylic acid (I) upon emulsifying it.

When the aqueous dispersion or solution is used as the sizing agent for papers, the sizing agent is added to a pulp slurry, and as occasion demands, known additives generally used in paper making such as aluminum sulfate, a filler, a fixing agent, a paper strengthening agent and a retention agent for filler may be further added. The amount of the sizing agent is usually from 0.01 to 2.0% by weight (calculated as the solid matter in the agent), preferably from 0.02 to 1.0% by weight based on the weight of the pulp. When the amount of the sizing agent is less than 0.01% by weight, it is difficult to exhibit the sizing effect satisfactorily. On the other hand, even if the amount is more than 2.0% by weight, the effect owing to excessive amount of the sizing agent is not expected.

As the filler used in the invention, any usual one such as clay, talc, calcium carbonate, titanium dioxide or bentonite can be employed without particular limitations. Especially, in case of the paper making under a condition of pH 6 to 9, alkaline fillers such as calcium carbonate, which is cheap but cannot be used in the conventional acidic paper making, can be suitably used, thus resulting in greatly lowering costs for paper making.

Any known fixing agents and paper strengthening agents can be used in the sizing process of the invention. Examples of the fixing agent or the paper strengthening agents are, for instance, a cationized starch, a polyamide-polyamine resin modified with epichlorohydrin, a dicyandiamide resin modified with epichlorohydrin, a styrene-dimethylaminoethyl methacrylate copolymer modified with epichlorohydrin, a modified polyacrylamide by Mannich reaction, an acrylamide-dimethylaminoethyl methacrylate copolymer, a compound obtained by Hofmann degradation of polyacrylamide, a copolymer of dialkyldiallyl ammonium chloride and sulfur dioxide, and the like.

The paper sizing agent of the present invention can exhibit excellent sizing effects even if using it alone. Also, the sizing agent can be used in combination with other known sizing agents such as soaps or dispersions of fortified rosins, soaps of fatty acids, hydrolyzed addition products of an olefin oligomer with succinic anhydride, a styrene-dimethylaminoethyl-methacrylate copolymer modified with epichlorohydrin, an alkenyl succinic anhydride, an alkyl ketene dimer and a condensation product of a fatty acid and polyalkylenepolyamine modified with epichlorohydrin.

The paper sizing agent of the invention can be suitably used in paper making under the condition of the wide pH-range from acidic to alkaline conditions, i.e. usually pH 3 to 9, and can sufficiently exhibit the excellent sizing effect. Further, the sizing agent of the invention can be used as a surface sizing agent.

The present invention is more specifically described and explained by means of the following Examples and Comparative Examples, in which all % and parts are by weight unless otherwise noted. It is to be understood that the present invention is not limited to the Examples, and various changes and modifications may be made in the invention without departing from the spirit and scope thereof.

EXAMPLES 1 to 15

There was dissolved 100 parts of each effective component shown in Table 1 with heating in 100 parts of toluene and 12 parts of an emulsifier (polyoxyethylene alkyl phenyl ether, commercially available under the trade name "NOIGEN EA-120" made by DAI-ICHI KOGYO SEIYAKU CO., LTD.). To the mixture was added 9,800 parts of warm water of a temperature of 90° C., which was stirred at high speed (17,000 rpm) to give an aqueous dispersion having a solid concentration of 1%.

Paper making was carried out according to the following methods using each obtained aqueous dispersion which was the sizing agent of the present invention, then the sizing effect was measured.

(1) Alkaline paper making

To a 1% slurry of a L-BKP pulp beaten to 450 ml of Canadian standard freeness were added calcium carbonate in an amount of 20% (calculated as solid matter) based on the weight of the pulp as a filler, aluminum sulfate in an amount of 1% (calculated as solid matter) based on the weight of the pulp and cationized starch (commercially available under the trade name "Cato 15" made by Oji National Company, LTD) in an amount of 1% (calculated as solid matter) based on the weight of the pulp, to which the sizing agent obtained in each of Examples 1 to 15 in an amount of 0.2% (calculated as solid matter) based on the weight of pulp and anionic polyacrylamide (commercially available under the trade name "KW-504" made by Arakawa Kagaku Kogyo Kabushiki Kaisha) in an amount of 0.02% (calculated as solid matter) based on the weight of pulp as a retention agent for filler were added, and the mixture was dispersed uniformly. The obtained pulp slurry had a pH of 7.8. The slurry was subjected to paper making by using a TAPPI standard sheet machine to give a sheet having a basis weight of 70 g/m$^2$.

(2) Acidic paper making

To a 1% pulp slurry obtained in the same manner as in the alkaline paper making was added aluminum sulfate in an amount of 3% (calculated as solid matter) based on the weight of pulp, and then the sizing agent obtained in each of Examples 1 to 15 in an amount of 0.2% (calculated as solid matter) based on the weight of the pulp and the mixture was dispersed uniformly. The obtained pulp slurry had a pH of 4.5. The slurry was subjected to paper making in the same manner as in the alkaline paper making.

The wet sheet obtained by each of the above-mentioned methods (1) and (2) was pressed to dehydrate and dried at 100° C. for 1 minute.

After conditioning the sheet for 24 hours under the condition provided in Japanese Industrial Standard (JIS) P 8111 (Conditioning of Paper and Paperboard for Test), the sizing effect [the sizing degree (second)] was measured according to a Stockigt method (JIS P 8122).

The results are shown in Table 1.

Comparative Examples 1 to 4

The procedure of Example 1 was repeated except that each effective component for comparison shown in Table 1 was used to prepare an aqueous dispersion having a solid concentration of 1%. After carrying out paper making, the sizing effect was measured in the same manner as in Example 1. The results are shown in Table 1.

Comparative Examples 5 to 7

Paper making was carried out in the same manner as in Example 1 except that each sizing agent put on the market shown in Table 1 was used. The sizing effect was measured in the same manner as in Example 1. The results are shown in Table 1.

over the wide pH-range, i.e., pH 3 to 9, and has the excellent storage stability (hydrolysis resistance).

Also, the method for sizing papers of the present invention is excellent in the workability and high in the industrial value since the method has no defect that the sizing effect is very slow to exhibit as in the sizing method using the alkyl ketene dimer sizing agent, or it is necessary to emulsify the sizing agent just before it is added to the paper furnish as in the sizing method using the alkenyl succinic anhydride.

In addition to the ingredients used in the Examples, other ingredients can be used in the Examples as set forth in the specification to obtain substantially the same results.

What we claim is:

1. A method for sizing paper which comprises mixing a pulp slurry with a sizing agent comprising an aqueous dispersion having a solids content of 0.5 to 70% by weight, said solids comprising 80–99% by weight of an α-hydroxycarboxylic acid, or a salt thereof, and 20–1% by weight of an emulsifier, to form a mixture containing 0.1 to 1.0% of said solids based on the weight of the pulp, and preparing paper from the mixture;

said α-hydroxycarboxylic acid having the formula (I)

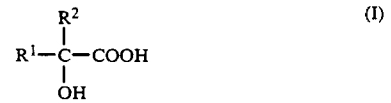

TABLE 1

| | Effective component in the sizing agent | Sizing degree (second) | |
|---|---|---|---|
| | | Paper making under the condition of pH 7.8 | Paper making under the condition of pH 4.5 |
| Ex. No. | | | |
| 1 | 2-Hydroxystearic acid | 42.3 | 39.5 |
| 2 | 2-Hydroxypalmitic acid | 40.1 | 38.4 |
| 3 | 2-Hydroxybehenic acid | 38.5 | 35.3 |
| 4 | 2-Hydroxymyristic acid | 30.1 | 24.2 |
| 5 | Mixture of 2-hydroxystearic acid and 2-hydroxypalmitic acid in the mixing ratio of 1:1 | 44.7 | 40.8 |
| 6 | Dipentadecyl hydroxyacetic acid | 37.2 | 28.5 |
| 7 | 2-Hydroxy-3-octadecyloxycarbonyl-propionic acid | 30.7 | 25.8 |
| 8 | 2-Hydroxy-3-hexadecyloxycarbonyl-propionic acid | 29.8 | 22.7 |
| 9 | 2-Hydroxy-3-octadecylaminocarbonyl-propionic acid | 25.4 | 26.8 |
| 10 | 2,3-Dihydroxy-3-octadecyloxycarbonyl-propionic acid | 38.5 | 33.4 |
| 11 | 2,3-Dihydroxy-3-hexadecyloxycarbonyl-propionic acid | 35.3 | 30.1 |
| 12 | 2,3-Dihydroxy-3-octadecylaminocarbonyl-propionic acid | 27.7 | 24.8 |
| 13 | N-(hydroxycarboxy)methylstearamide | 36.1 | 35.4 |
| 14 | N-(hydroxycarboxy)methylpalmitamide | 32.2 | 36.6 |
| 15 | Triethanolamine salt of 2-hydroxypalmitic acid | 44.9 | 40.7 |
| Com Ex. | | | |
| 1 | Stearic acid | 4.7 | 28.5 |
| 2 | Palmitic acid | 2.5 | 22.1 |
| 3 | Monostearyl maleate | 0 | 10.8 |
| 4 | Monostearyl succinate | 0 | 11.1 |
| 5 | Alkyl ketene dimer sizing agent[*1] | 50.0 | 8.3 |
| 6 | Dispersion of a fortified rosin[*2] | 0 | 37.1 |
| 7 | Metal salt of alkenyl succinic acid[*3] | 0 | 35.2 |

(Notes)
[*1] Commercially available under the trade name "Sizepine K-902" made by Arakawa Kagaku Kogyo Kabushiki Kaisha
[*2] Commercially available under the trade name "Sizepine N-705" made by Arakawa Kagaku Kogyo Kabushiki Kaisha
[*3] Commercially available under the trade name "Sizepine S-300" made by Arakawa Kagaku Kogyo Kabushiki Kaisha The paper sizing agent of the present invention can exhibit the excellent sizing effect in the paper making wherein $R^1$ is an alkyl group having 8 to 30 carbon atoms, an alkenyl group having 8 to 30 carbon atoms, a group having the formula (IIa):

$$R^3-X-\overset{\overset{O}{\|}}{C}-CH_2-\qquad(IIa)$$

in which $R^3$ is an alkyl group having 8 to 30 carbon atoms or an alkenyl group having 8 to 30 carbon atoms and X is an oxygen atom or —NH—, a group having the formula (IIb):

$$R^3-X-\overset{\overset{O}{\|}}{C}-\overset{\overset{OH}{|}}{CH}-\qquad(IIb)$$

in which $R^3$ and X are as defined above; or a group having the formula (IIc):

$$R^3-\overset{\overset{O}{\|}}{C}-NH-\qquad(IIc)$$

in which $R^3$, is as defined above; and $R^2$ is a hydrogen atom, an alkyl group having 1 to 30 carbon atoms or an alkenyl group having 1 to 30 carbon atoms.

2. The method of claim 1, wherein said α-hydroxycarboxylic acid is an α-hydroxyalkanoic acid.

3. The method of claim 1, wherein said α-hydroxycarboxylic acid is a dialkyl hydroxyacetic acid.

4. The method of claim 1, wherein said α-hydroxycarboxylic acid is a monoester of malic acid.

5. The method of claim 1, wherein said α-hydroxycarboxylic acid is a monoester of tartaric acid.

6. The method of claim 1, wherein said α-hydroxycarboxylic acid is an amido glycolic acid.

7. The method of claim 1, wherein said emulsifier is a surfactant.

8. The method of claim 1, wherein said emulsifier is a protective colloid.

9. The method of claim 7, wherein said surfactant is at least one member selected from the group consisting of an anionic surfactant, a nonionic surfactant and a cationic surfactant.

10. The method of claim 9, wherein said surfactant is at least one member selected from the group consisting of an alkylbenzenesulfonate, an alkylsulfate, a rosined soap, a polyoxyethylene alkylphenyl ether sulfate, a polyoxyethylene alkylphenyl ether sulfonate, a polyoxyethylene alkylphenol ether sulfosuccinate, a polyoxyethylene distyrylpheny ether sulfate, a polyoxyethylene distyrylphenyl ether sulfosuccinate, polyethylene oxide, polypropylene oxide, alkyl, aryl, alkylaryl and aralkylaryl esters of polyethylene oxide; alkyl, aryl, alkylaryl and aralkylaryl partial esters of polyethylene oxide; alkyl, aryl, alkylaryl and aralkylaryl ethers of polyethylene oxide; alkyl, aryl, alkylaryl and aralkylaryl amides of polyethylene oxide; alkyl, aryl, alkylaryl and aralkylaryl esters of polypropylene oxide; alkyl, aryl, alkylaryl and aralkylaryl partial ethers of polypropylene oxide; alkyl, aryl, alkylaryl and aralkylaryl partial ethers of polypropylene oxide; alkyl, aryl, alkylaryl and aralkylarlyl amides of polypropylene oxide; lauryltrimethylbenzylammonium chloride, sterayltrimethylbenzylammonium chloride, disteraryldimethylammonium chloride, alkyklbenzyldimethylammonium chloride and alkylpyridinium chloride.

11. The method of claim 8, wherein said protective colloid is at least one member selected from the group consisting of casein, lecithin, polyvinyl alcohol, a salt of styrene-maleic anhydride copolymer, a salt of styrene-acrylic acid copolymer and a modified starch.

12. The method of claim 1, wherein said α-hydroxycarboxylic acid is neutralized with a hydroxide of an alkali metal, ammonium or an alkanol amine.

* * * * *